United States Patent [19]
Venkateshwaran et al.

[11] Patent Number: 5,985,317
[45] Date of Patent: Nov. 16, 1999

[54] PRESSURE SENSITIVE ADHESIVE MATRIX PATCHES FOR TRANSDERMAL DELIVERY OF SALTS OF PHARMACEUTICAL AGENTS

[75] Inventors: Srinivasan Venkateshwaran; David Fikstad; Charles D. Ebert, all of Salt Lake City, Utah

[73] Assignee: TheraTech, Inc., Salt Lake City, Utah

[21] Appl. No.: 08/706,624

[22] Filed: Sep. 6, 1996

[51] Int. Cl.⁶ .................................................. A61L 15/16
[52] U.S. Cl. ........................ 424/449; 424/447; 424/448
[58] Field of Search .................... 424/448, 449, 424/447

[56] References Cited

U.S. PATENT DOCUMENTS

| | | | |
|---|---|---|---|
| 4,201,211 | 5/1980 | Chandrasekaran et al. | 128/268 |
| 4,262,003 | 4/1981 | Urquhart et al. | 424/267 |
| 4,409,206 | 10/1983 | Stricker | 424/81 |
| 4,564,010 | 1/1986 | Coughlan et al. | 128/156 |
| 4,645,502 | 2/1987 | Gale et al. | 604/896 |
| 4,863,970 | 9/1989 | Patel et al. | 514/784 |
| 4,904,475 | 2/1990 | Gale et al. | 424/449 |
| 4,956,171 | 9/1990 | Chang | 424/449 |
| 5,002,773 | 3/1991 | Keshary et al. | 424/448 |
| 5,149,538 | 9/1992 | Granger | 424/449 |
| 5,186,938 | 2/1993 | Sablotsky et al. | 424/443 |
| 5,230,896 | 7/1993 | Yeh et al. | 424/443 |
| 5,310,559 | 5/1994 | Shah | 424/448 |
| 5,368,860 | 11/1994 | Sunami | 424/448 |
| 5,589,498 | 12/1996 | Mohr | 514/413 |
| 5,633,009 | 5/1997 | Kenealy | 424/448 |

OTHER PUBLICATIONS

R. J. Scheuplein, Permeability of the Skin, 51, Physiological Reviews, 702–47 (1972).

*Primary Examiner*—Thurman K. Page
*Assistant Examiner*—Kathryne E. Shelborne
*Attorney, Agent, or Firm*—Thorpe, North & Western, L.L.P.

[57] ABSTRACT

A method of transdermally or transmucosally delivering a hydrophilic salt form of a drug with a water-based pressure sensitive hydrophobic adhesive matrix patch optionally containing a permeation enhancer is disclosed. A matrix patch comprising a water-based pressure sensitive hydrophobic adhesive, a hydrophilic salt form of a drug, and optionally a permeation enhancer for transdermal or transmucosal delivery of the hydrophilic salt form of the drug is also disclosed.

18 Claims, 1 Drawing Sheet

PRESSURE SENSITIVE ADHESIVE MATRIX PATCHES FOR TRANSDERMAL DELIVERY OF SALTS OF PHARMACEUTICAL AGENTS

BACKGROUND OF THE INVENTION

This invention relates to compositions and methods for delivery of drugs. More particularly, the invention relates to pressure sensitive adhesive matrix patches and methods of use thereof for transdermal delivery of hydrophilic salts of pharmaceutical agents.

Transdermal delivery of various drugs is well known in the art of drug delivery. Pressure sensitive adhesive matrix patches for transdermal delivery of drugs are also known in the art. These matrix patches typically include an inert, impervious backing layer, a pressure sensitive adhesive layer containing the drug and optional selected excipients, and a release liner that is peeled off and discarded before applying the patch to the skin. Suitable pressure sensitive adhesives include polysiloxanes, polyacrylates, polyisobutylene, and the like. These pressure sensitive adhesive polymers are very hydrophobic and are typically purchased as solutions of polymer dissolved in organic solvents. The drug and selected excipients, if any, are directly incorporated into the organic-solvent-based pressure sensitive adhesive solution, mixed, cast as a thin film, and dried to evaporate the solvents, leaving a dried adhesive matrix film containing the drug and excipients. It is well known in the art that the drug has to be hydrophobic to be incorporated into the organic-solvent-based, hydrophobic adhesive. Hydrophilic salt forms of a drug are generally not compatible with such organic-solvent-based pressure sensitive adhesives and have to be converted to the more hydrophobic free acid or free base form for incorporation into the organic-solvent-based, hydrophobic adhesive.

Keshary et al., U.S. Pat. No. 5,002,773, describe transdermal delivery of a calcium antagonist compound, "TA-3090," to patients in need of a calcium channel blocking effect. Keshary et al. state that the free base form of TA-3090 can generally be incorporated in polymeric matrix materials in a higher percent by weight than the maleate salt form of TA-3090 and that the free base form is preferred for transdermal delivery. Chandrasekaran et al., U.S. Pat. No. 4,201,211, disclose a gelled mineral oil-polyisobutylene-clonidine free base skin patch for antihypertensive effect, whereas the hydrochloride salt is used in the manufacture of oral clonidine tablets. Urquhart et al., U.S. Pat. No. 4,262,003, describe a gelled mineral oil-polyisobutylene-scopolamine free base transdermal patch for the administration of scopolamine base to inhibit nausea and emesis. These examples illustrate the conversion of a hydrophilic salt form of a drug into the more hydrophobic free base form to render it more compatible for incorporation into a hydrophobic pressure sensitive adhesive matrix patch.

Water-based pressure sensitive adhesives are also commercially available. These water-based adhesives are formulated as emulsions wherein the hydrophobic pressure sensitive adhesive polymer is dispersed in water with the help of surfactants. Such water-based adhesives provide inherent advantages of safety and reduced environmental problems over solvent-based pressure sensitive adhesives, because the carrier is water and not an organic solvent. These water-based adhesives are widely used in the manufacture of medical tapes and bandages, and provide excellent skin adhesion.

Coughlan et al., U.S. Pat. No. 4,564,010, disclose a pressure sensitive adhesive film for medical use comprising a base layer laminated to a water-based pressure sensitive adhesive coating formed of a mixture of a polyacrylic latex, an ester resin, and a thickening agent. Coughlan et al. teach that such films can be used in transdermal delivery systems, however, they fail to describe the types of drugs that may be suitable for transdermal delivery with such a system. Yeh et al., U.S. Pat. No. 5,230,896, describe a transdermal delivery system for administration of nicotine comprising nicotine base, an acrylic polymer adhesive, a stabilizer, and a polyester film backing. It is stated that a nicotine salt is also contemplated in the practice of the invention. Such a nicotine salt is used to reduce volatility of the drug and is formed in situ by addition of acid. When an acid is used to produce the nicotine salt, an emulsion thickener is also required to increase the viscosity of the formulation. Nicotine is a unique compound in that both the free base and its salt forms are very water soluble. Sablotsky et al., U.S. Pat. No. 5,186,938, describe the use of a water-based emulsion adhesive patch for the transdermal administration of nitroglycerin.

Hydrophilic salt forms of hydrophobic drugs are generally readily soluble in water-based pressure sensitive adhesives because the solvent is water, not an organic solvent. What has hitherto gone unrecognized, and is the subject matter of the present invention, is that the hydrophilic salt form of a hydrophobic drug can not only be readily incorporated into the water-based hydrophobic pressure sensitive adhesive, but that the drug is then readily permeable across skin from the dried adhesive film. In fact, the skin flux of the hydrophilic salt form of a drug from a water-based pressure sensitive adhesive matrix is comparable to that of the hydrophobic free base or free acid form from an organic solvent-based pressure sensitive adhesive matrix patch. This finding is novel and contrary to conventional wisdom, which holds that hydrophilic compounds are much less permeable across skin than more hydrophobic substances. R. J. Scheuplein et al., Permeability of the Skin, 51 Physiological Reviews 702–47 (1972); G. L. Flynn, Mechanisms of Percutaneous Absorption from Physicochemical Evidence, in Percutaneous Absorption 27–51 (R. L. Bronaugh & H. I. Maibach eds., Marcel Decker, Inc. 1989). Gale et al., U.S. Pat. Nos. 4,645,502 and 4,904,475, disclose a reservoir patch device for transdermal delivery of highly ionized, fat-insoluble drugs. This invention is premised on the observation that unionized forms of most drugs are more permeable through skin than their ionized forms, i.e. the salt of a particular drug generally cannot be delivered through skin without significant permeation enhancement. For example, Keshary et al., U.S. Pat. No. 5,002,773, show that the free base form of TA-3090 is 7–10 fold more permeable than the maleate salt of TA-3090 from organic solvent based pressure sensitive adhesive matrix systems. In view of the foregoing, it will be appreciated that compositions and methods for efficient transdermal delivery of hydrophilic salt forms of drugs with hydrophobic pressure sensitive matrix patches would be a significant advancement in the art.

BRIEF SUMMARY OF THE INVENTION

It is an object of the present invention to provide pressure sensitive adhesive matrix patches and methods of use thereof for transdermal and/or transmucosal delivery of hydrophilic salts of pharmaceutical agents.

It is also an object of the invention to provide adhesive matrix patches and methods of use thereof that are compatible with hydrophilic salt forms of pharmaceutical agents for transdermal and/or transmucosal delivery thereof.

It is another object of the invention to provide permeation enhanced transdermal and/or transmucosal delivery of hydrophilic salts of pharmaceutical agents with water-based pressure sensitive adhesive matrix patches.

These and other objects can be achieved by providing a method of transdermally delivering a hydrophilic salt form of a drug comprising the steps of:

(a) providing a pressure sensitive adhesive matrix patch device comprising a drug-containing adhesive matrix layer comprising a water-based polymeric adhesive having dissolved therein an effective amount of the hydrophilic salt form of the drug, and optionally an effective amount of a permeation enhancer, a proximal surface of the layer adapted to adhere to the skin and a distal surface of the layer adapted to adhere to a backing layer, and a backing layer that is substantially impermeable to the drug laminated to the distal surface; and (b) contacting a selected area of the skin with the matrix patch device such that the proximal surface of the drug-containing adhesive matrix layer adheres to and is in drug transfer relationship with the selected area of the skin.

Preferred water-based adhesives include acrylic and polyisobutylene adhesives, and preferred drugs include ketorolac tromethamine, diclofenac sodium, buspirone HCl, lidocaine HCl, and clonidine HCl. Preferred permeation enhancers include cell envelope disordering compounds, solvents, and mixtures thereof.

A pressure sensitive adhesive matrix patch device for transdermally delivering a hydrophilic salt form of a drug comprises a drug-containing adhesive matrix layer comprising a water-based adhesive having dissolved therein an effective amount of the hydrophilic salt form of the drug, and optionally an effective amount of a permeation enhancer, a proximal surface of the layer adapted to adhere to the skin and a distal surface of the layer adapted to adhere to a backing layer, and a backing layer that is substantially impermeable to the drug laminated to the distal surface.

DETAILED DESCRIPTION

Figure 1:
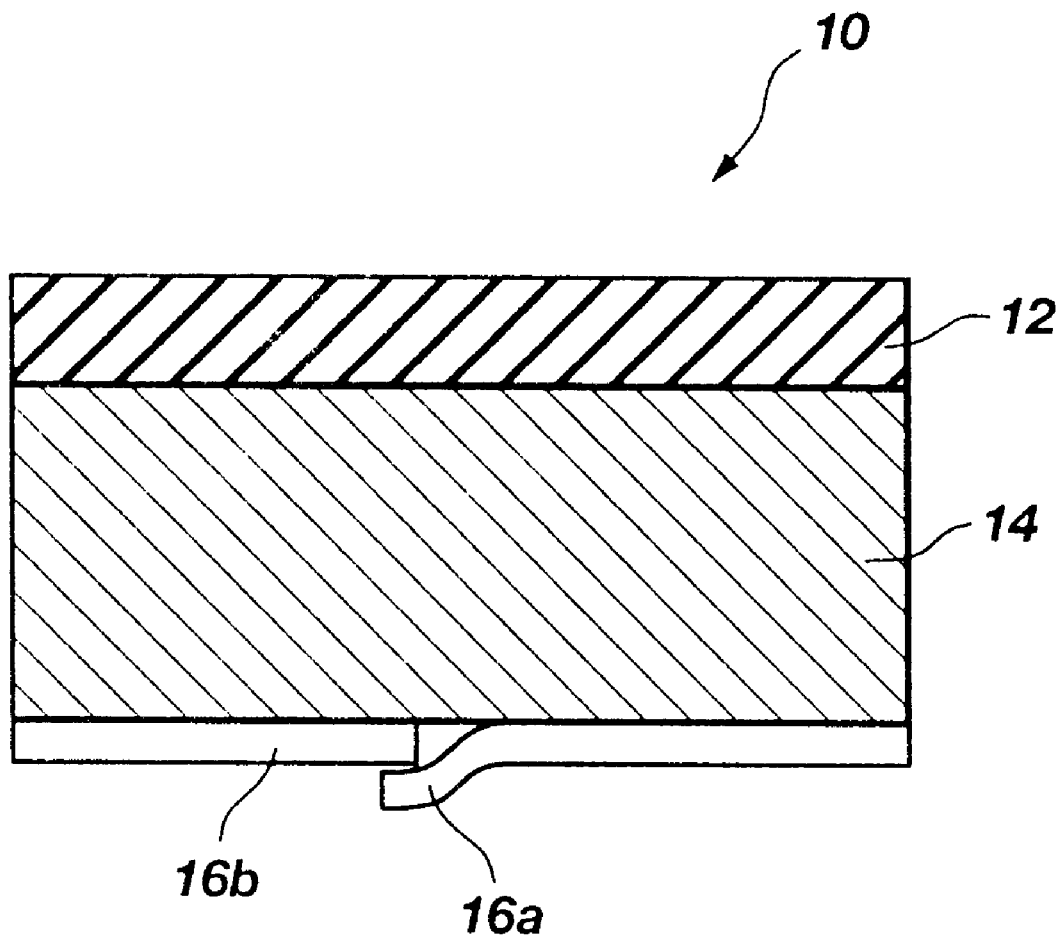
FIG. 1 shows a schematic sectional view through an illustrative device according to the present invention.

Before the present composition and method of use thereof for transdermal delivery of hydrophilic salts of pharmaceutical agents are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a composition for delivering "a drug" includes reference to two or more of such drugs, reference to "an adhesive" includes reference to one or more of such adhesives, and reference to "a permeation enhancer" includes reference to two or more of such permeation enhancers.

In describing and claiming the present invention, the following terminology will be used in accordance with the definitions set out below.

As used herein, "hydrophilic salt form" and similar terms mean an ionic form of a drug or pharmaceutical agent, such as sodium, potassium, ammonium, tromethamine, or other cation salts thereof, sulfate or other anion salts thereof, acid addition salts of basic drugs, and base addition salts of acidic drugs. Illustrative examples of such salts include sodium diclofenac, sodium cromolyn, sodium acyclovir, sodium ampicillin, ketorolac tromethamine, amiloride HCl, ephedrine HCl, loxapine HCl, thiothixene HCl, trifluoperizine HCl, naltrexone HCl, naloxone HCl, nalbuphine HCl, buspirone HCl, bupriprion HCl, phenylephrine HCl, tolazoline HCl, chlorpheniramine maleate, phenylpropanolamine HCl, clonidine HCl, dextromethorphan HBr, metoprolol succinate, metoprolol tartrate, epinephrine bitartrate, ketotofin fumarate, atropine sulfate, fentanyl citrate, apomorphine sulfate, propranolol HCl, pindolol HCl, lidocaine HCl, tetracycline HCl, oxytetracycline HCl, tetracaine HCl, dibucaine HCl, terbutaline sulfate, scopolamine HBr, and brompheniramine maleate.

As used herein, "effective amount" means an amount of a drug or pharmacologically active agent that is nontoxic but sufficient to provide the desired local or systemic effect and performance at a reasonable benefit/risk ratio attending any medical treatment. An effective amount of a permeation enhancer as used herein means an amount selected so as to provide the selected increase in skin permeability and, correspondingly, the desired depth of penetration, rate of administration, and amount of drug delivered.

As used herein, "transdermal" refers to delivery of a drug through the skin or mucosa and thus includes transmucosal. Similarly, "skin" is meant to include mucosa. Such mucosa include, without limitation, the buccal, nasal, rectal, and vaginal mucosa.

As used herein, "drug," "pharmaceutical agent," "pharmacologically active agent," or any other similar term means any chemical or biological material or compound suitable for transdermal administration by the methods previously known in the art and/or by the methods taught in the present invention that induces a desired biological or pharmacological effect, which can include but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating the disease from the organism. The effect can be local, such as providing for a local anaesthetic effect, or it can be systemic. This invention is not drawn to novel drugs or new classes of active agents. Rather it is limited to the mode of delivery of agents or drugs that exist in the state of the art or that may later be established as active agents and that are suitable for delivery by the present invention. Such substances include broad classes of compounds normally delivered into the body, including through body surfaces and membranes, including skin. In general, this includes but is not limited to: antiinfectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral, and cerebral; central nervous system stimulants; vasoconstrictors; cough and cold preparations, including decongestants; hormones such as estradiol and other steroids, including corticosteroids; hypnotics; immunosuppressives; muscle relaxants; parasympatholytics; psychostimulants; sedatives; and tranquilizers. By the method of the present invention, ionized drugs can be delivered, as can drugs of either high or low molecular weight.

As used herein, "permeation enhancer," "penetration enhancer," "chemical enhancer," or similar terms refer to compounds and mixtures of compounds that enhance the flux of a drug across the skin. Flux can be increased by changing either the resistance (the diffusion coefficient) or the driving force (the gradient for diffusion).

Chemical enhancers are comprised of two primary categories of components, i.e., cell-envelope disordering compounds and solvents or binary systems containing both cell-envelope disordering compounds and solvents. The latter are well known in the art, e.g. U.S. Pat. Nos. 4,863,970 and 4,537,776, incorporated herein by reference.

Cell envelope disordering compounds are known in the art as being useful in topical pharmaceutical preparations. These compounds are thought to assist in skin penetration by disordering the lipid structure of the stratum corneum cell-envelopes. A comprehensive list of these compounds is described in European Patent Application 43,738, published Jun. 13, 1982, which is incorporated herein by reference. Examples of cell envelope disordering compounds that can be used as enhancers, without limitation, include saturated and unsaturated fatty acids and their esters, alcohols, monoglycerides, acetates, diethanolamides, and N,N-dimethylamides, such as oleic acid, propyl oleate, isopropyl myristate, glycerol monooleate, glycerol monolaurate, methyl laurate, lauryl alcohol, lauramide diethanolamide, and mixtures thereof. Saturated and unsaturated sorbitan esters, such as sorbitan monooleate and sorbitan monolaurate, can also be used. It is believed that any cell envelope disordering compound is useful for purposes of this invention.

Suitable solvents include water; diols, such as propylene glycol and glycerol; mono-alcohols, such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones (azones) and the like.

The present invention is based on the discovery that pressure sensitive adhesive matrix patches can be formulated for transdermal delivery of the hydrophilic salt form of a drug, wherein equivalent skin flux is obtained as compared to patches formulated with the free acid or free base form of the drug in an organic solvent-based pressure sensitive adhesive.

The salt form of the drug is usually hydrophilic and insoluble in organic-solvent-based adhesives and cannot be incorporated into such organic-solvent-based adhesive patches to provide clinically meaningful skin flux. Such salt forms of drugs have previously had to be converted to the more hydrophobic free acid or free base form to be soluble and/or compatible in the organic-solvent-based adhesive to obtain clinically meaningful skin flux. This prior art procedure requires additional process steps, wherein the drug is converted from the FDA approved salt form to an unapproved free acid or free base form, thus introducing additional regulatory and/or toxicological hurdles to developing a matrix patch. These problems can be avoided by formulating the salt form of the drug in a water-based pressure sensitive adhesive such that skin flux equivalent to that of patches formulated with the free acid or free base form of the drug in an organic-solvent-based pressure sensitive adhesive is obtained.

FIG. 1 shows an exemplary matrix patch 10 that is compatible with the present invention. The patch 10 is a laminated composite in which the backing layer 12 forms the top surface of the composite. The drug-containing adhesive matrix layer 14 is immediately below and adjacent to the backing layer. Prior to use, the laminate also includes a strippable protective release liner. The release liner can be in the form of two sheets, 16a and 16b, the first sheet 16a partially overlapping the second sheet 16b. Additional structural layers can also be present.

The backing layer, which adheres to the drug-containing adhesive layer serves as the upper layer of the device during use and functions as the primary structural element of the device. The backing layer is made of a sheet or film of a preferably flexible elastomeric material that is substantially impermeable to the drug and any enhancer that may be present. This backing layer is typically about 0.001–0.004 inch in thickness and is preferably of a material that permits the device to follow the contours of the skin such that it can be worn comfortably on any skin area including joints or other areas of flexure. In this way, in response to normal mechanical strain, there is little or no likelihood of the device disengaging from the skin due to differences in the flexibility or resiliency of the skin and the device. Examples of polymers useful for the backing layer are polyethylene, polypropylene, polyesters, polyurethanes, polyethylene vinyl acetate, polyvinylidene chloride, block copolymers such as PEBAX, and the like. The backing layer can also comprise laminates of one or more of the foregoing polymers.

The release liner is a disposable element that serves only to protect the device prior to application to the skin. Typically, the release liner is formed from a material impermeable to the drug, enhancer, and other components of the device, and is easily strippable from the pressure sensitive adhesive. Release liners can generally be made of the same materials as the backing layer.

The drug-containing adhesive matrix layer can, in addition to the water-based or water-borne adhesive, drug, and optional permeation enhancer, also contain other optional ingredients, such as carriers, vehicles, excipients, diluents, and the like, which are materials without pharmacological activity that are suitable for administration in conjunction with the presently disclosed and claimed compositions. Such materials are pharmaceutically acceptable in that they are nontoxic, do not interfere with drug delivery, and are not for any other reasons biologically or otherwise undesirable. The pressure sensitive adhesives used in accordance with the present invention must also be pharmaceutically acceptable. Examples of illustrative materials include water, mineral oil, silicone, inorganic gels, aqueous emulsions, liquid sugars, waxes, petroleum jelly, and a variety of other oils and polymeric materials.

Adhesive Matrix Preparation

Pressure sensitive adhesive matrix systems were prepared as follows. First, the solids content of a selected water-based or solvent-based adhesive solution was determined by placing a known weight of solution in a weighed aluminum dish and evaporating the solvents overnight in a 70° C. convection oven. The content of solid adhesive in the solution was calculated by dividing the adhesive solid weight after drying by the initial total solution weight. For the preparation of polyisobutylene (PIB) adhesives in an organic solvent, solid PIB was first dissolved in heptane to achieve a final solid content of about 30% by weight, and then the exact solid content was determined as described above. Next, a weighed quantity of adhesive solution was added to a glass bottle, and the solid adhesive weight was calculated from the known solid fraction of the given adhesive solution. The drug substance (hydrophilic salt or free acid or free base) was weighed and added to the adhesive solution in a quantity necessary to achieve a selected dry matrix film composition. The solution containing the adhesive polymer drug substance was then mixed overnight. In some cases, the drug substance dissolved completely in the adhesive solution. In other cases, the drug did not completely dissolve, resulting in a liquid containing some drug crystals dispersed in the solution. After mixing, approximately 8 ml of the solution was dispensed on a silanized polyester release liner and film cast using a casting knife with a gap size appropriate to achieve a final dried thickness of approximately 0.05–0.1 mm. The cast was dried in a 70° C. convection oven for 15–30 minutes to yield a dried matrix onto which an 0.08 mm thick polyethylene backing film was laminated. These matrix systems were then used to conduct in vitro skin flux experiments as described below.

Skin Flux Studies

In vitro skin flux studies were conducted using human cadaver epidermal membrane in modified Franz non-jacketed diffusion cells. The epidermal membrane (stratum corneum and epidermis) was separated from whole skin (epidermal membrane and dermis) by the heat-separation method of Kligman & Christopher, 88 Arch. Dermatol. 702 (1963). This method involves the exposure of the full-thickness skin to water at 60° C. for 60 seconds. After this period, the epidermal membrane was gently peeled from the dermis and stored in aluminum foil at −5° C. Prior to skin permeation experiments, the silanized release liner was removed from the adhesive matrix system, and the adhesive was affixed to the stratum corneum side of the thawed epidermal membrane, which was then cut to an appropriate size and placed between the two halves of the diffusion cell with the stratum corneum facing the donor compartment.

The receiver compartment was filled with water or an aqueous buffer appropriate to maintain sink conditions for the drug. All receiver media included 0.02% (w/w) sodium azide to inhibit bacterial growth. The diffusion cell was placed in a temperature controlled circulating water bath calibrated to maintain the surface temperature of the skin at 32° C. The receiver compartment was constantly stirred by a magnetic stir bar in the receiver compartment agitated by a magnetic stirring module placed under the water bath. At predetermined sampling intervals, the entire contents of the receiver compartment were collected for drug quantitation, and the receiver compartment was filled with fresh receiver solution, taking care to eliminate any air bubbles at the skin/solution interface.

The cumulative amount of drug permeated per unit area at any time t ($Q_t$, $\mu g/cm^2$) was determined according to the following equation:

$$Q_t = \sum_{t=0}^{t} \frac{C_t V}{A}$$

where $C_t$ ($\mu g/cm^3$) is the concentration of the receiver compartment at sample time t (hours), V is the volume of the receiver compartment of the diffusion cell (6.3 cm$^3$), and A is the diffusional area of the cell (0.64 cm$^2$)

EXAMPLE 1

Ketorolac is an acidic non-steroidal anti-inflammatory drug, and the FDA-approved form of ketorolac is the hydrophilic tromethamine salt (2-amino-2-hydroxymethyl-1,3-propanediol). Pressure sensitive matrix systems with ketorolac free acid and ketorolac tromethamine were prepared in an organic solvent-based acrylic pressure sensitive adhesive (TSR; Sekisui Chemical Co., Osaka, Japan) at concentrations equivalent to 1% (w/w) of the tromethamine salt. The tromethamine salt did not completely dissolve in the organic solvent system, and the final dried cast was a dispersion of crystallized drug in an acrylic adhesive matrix. Ketorolac free acid completely dissolved in the organic solvent system, and the final dried cast was visually free of any crystals. An adhesive matrix system with ketorolac tromethamine at 1% (w/w) was also prepared in a water-based acrylic adhesive (NACOR 72-9965; National Starch and Chemical Co., New Jersey). The tromethamine salt dissolved completely in the water/emulsion system, and the dried cast was free of any drug crystals. The results of in vitro skin flux experiments using these matrix systems are summarized in Table 1.

TABLE 1

| | In vitro Permeation of Ketorolac[a] | | |
|---|---|---|---|
| Skin | TSR/salt[b] | TSR/acid[c] | NACOR/salt[d] |
| 1 | 2.78 ± 1.78 (n = 5 cells) | 2.18 ± 0.85 (n = 4 cells) | 7.34 ± 3.75 (n = 5 cells) |
| 2 | 0.52 ± 0.23 (n = 5) | 1.04 ± 0.28 (n = 5) | 2.29 ± 0.46 (n = 5) |
| 3 | 0.72 ± 0.29 (n = 5) | 1.72 ± 0.72 (n = 5) | 8.13 ± 1.74 (n = 5) |
| 4 | 0.59 ± 0.37 (n = 5) | 1.56 ± 0.41 (n = 5) | 2.63 ± 0.87 (n = 5) |
| Total | 1.15 ± 1.29 (n = 20) | 1.59 ± 0.67 (n = 19) | 5.10 ± 3.35 (n = 20) |

[a]Mean ± SD, $\mu g/(cm^2 * 24\ h)$
[b]TSR/ketorolac tromethamine = 99%/1% (w/w)
[c]TSR/ketorolac free acid = 99%/0.7% (w/w)
[d]NACCR 72-9965/ketorolac tromethamine = 99%/1% (w/w)

Unexpectedly, the in vitro permeation from a matrix system prepared with the tromethamine salt of ketorolac in a water-based acrylic adhesive was twice that of a matrix system prepared with an equal concentration of the free acid in an organic solvent-based acrylic adhesive. In addition, permeation from a matrix prepared with the salt form dispersed in an organic solvent-borne acrylic adhesive was lower than permeation from the other two systems wherein the drug was dissolved rather than dispersed in the adhesive. This example demonstrates that the hydrophilic salt form of the drug in a water-based hydrophobic adhesive matrix yields a skin flux comparable to or greater than that obtained with the more hydrophobic, free acid form of the drug in an organic solvent-based adhesive matrix.

EXAMPLE 2

Diclofenac is an acidic non-steroidal anti-inflammatory drug. The FDA-approved form of diclofenac is the sodium salt. Diclofenac is considerably more hydrophobic than ketorolac (Example 1); water solubility of diclofenac free acid is <1 mg/ml. C. M. Adeyeye & L. Pui-Dai, Diclofenac Sodium, in 19 Analytical Profiles of Drug Substances (1990). Pressure sensitive matrix systems with diclofenac free acid and diclofenac sodium were prepared in the organic solvent-based acrylic adhesive, TSR, at molar concentrations equivalent to 1% or 2% (w/w) of diclofenac sodium. The sodium salt was not sufficiently soluble in the organic solvent system to dissolve completely, and the final dried cast was a dispersion of crystallized drug in an acrylic adhesive matrix. The free acid of diclofenac completely dissolved in the organic solvent system, and the final dried cast was visually free of drug crystals. Pressure sensitive adhesive matrix systems containing 1% or 2% (w/w) diclofenac sodium also were prepared in the water-borne acrylic adhesives NACOR 72-9965 and ROBOND PS20 (Rohm & Haas, Philadelphia, Pa.). The diclofenac sodium salt completely dissolved in these water-emulsion systems, and the dried cast was visually free of drug crystals. For the ROBOND PS20 adhesive it was necessary to add a thickening agent (2% KOLLIDON 90; BASF, Parsippany, N.J.) to achieve a viscosity adequate for wet film casting of the matrix. The results of in vitro skin flux experiments using these systems are summarized in Tables 2 and 3.

TABLE 2

| | No. | In vitro Permeation of Diclofenac[a] | | |
|---|---|---|---|---|
| Skin | Cells | TSR/salt[b] | TSR/acid[c] | NACOR/salt[d] |
| 1 | 5 | 0.87 ± 0.29 | 1.18 ± 0.13 | 4.40 ± 0.69 |
| 2 | 5 | 0.93 ± 0.45 | 0.97 ± 0.26 | 9.47 ± 2.92 |
| 3 | 5 | 0.60 ± 0.12 | 0.59 ± 0.14 | 7.38 ± 1.31 |
| 4 | 5 | 2.52 ± 1.07 | 1.47 ± 1.14 | 10.90 ± 6.18 |
| Total | 20 | 1.23 ± 0.95 | 1.05 ± 0.64 | 8.04 ± 4.07 |

[a]Mean ± SD, $\mu g/(cm^2 * 24\ h)$
[b]TSR/diclofenac sodium = 99%/1% (w/w)
[c]TSR/diclofenac free acid = 99.1%/0.9% (w/w)
[d]NACOR 72-9965/diclofenac sodium 99%/1% (w/w)

TABLE 3

| | No. | In vitro Permeation of Diclofenac[a] | | |
|---|---|---|---|---|
| Skin | Cells | TSR/salt[b] | TSR/acid[c] | ROBOND/salt[d] |
| 1 | 5 | 1.1 ± 0.2 | 2.5 ± 0.3 | 28.1 ± 5.4 |
| 2 | 5 | 0.5 ± 0.2 | 1.0 ± 0.2 | 14.3 ± 6.4 |
| 3 | 5 | 1.4 ± 1.4 | 3.4 ± 1.5 | 22.2 ± 3.8 |
| Total | 15 | 1.0 ± 0.9 | 2.3 ± 1.3 | 21.5 ± 7.6 |

[a]Mean ±, $\mu g/(cm^2 * 24\ h)$
[b]TSR/diclofenac sodium = 98%/2% (w/w)
[c]TSR/diclofenac = 98.2%/1.8% (w/w)
[d]ROBOND PS20/KOLLIDON 90/diclofenac sodium = 96%/2%/2% (w/w)

In vitro permeation from the matrix prepared with the sodium salt of diclofenac in the water-borne adhesives was significantly greater than that from the systems prepared with the organic solvent-based acrylic adhesive. These results demonstrate that the hydrophilic salt form of the drug in a water-based pressure sensitive adhesive matrix exhibits a skin flux comparable to or greater than that obtained with the more hydrophobic free acid form of the drug in an organic solvent-based adhesive matrix.

EXAMPLE 3

Buspirone is an anxiolytic drug, and the FDA-approved form of the drug is the hydrochloride (HCl) salt. Pressure sensitive matrix systems with buspirone free base were prepared in two organic solvent-based acrylic adhesives, TSR and DURO-TAK 2516 (National Starch and Chemical Co.), at concentrations equivalent to 1% or 2% (w/w) of the HCl salt. The HCl salt did not dissolve completely in these organic solvent-based adhesives, and the final dried casts were dispersions with visible solid drug crystals in the adhesive matrix. A matrix system with Buspirone HCl at 1% or 2% (w/w) was prepared in a water-based acrylic adhesive, NACOR 72-9965. The HCl salt dissolved completely in this adhesive solution, and the matrix was visibly free of drug crystals. The results of in vitro skin flux experiments using these systems are summarized in Tables 4–6.

TABLE 4

| | No. | In vitro Permeation of Buspirone[a] | | |
|---|---|---|---|---|
| Skin | Cells | TSR/salt[b] | TSR/base[c] | NACOR/salt[d] |
| 1 | 5 | 1.53 ± 0.70 | 15.54 ± 7.01 | 3.18 ± 0.50 |
| 2 | 5 | 4.46 ± 1.55 | 21.22 ± 4.36 | 9.16 ± 1.84 |
| 3 | 5 | 9.17 ± 4.95 | 27.40 ± 4.06 | 12.26 ± 2.67 |
| 4 | 5 | 4.02 ± 1.09 | 17.96 ± 1.37 | 9.54 ± 1.86 |
| Total | 20 | 4.80 ± 3.75 | 20.53 ± 6.25 | 8.53 ± 3.82 |

[a]Mean ± SD, $\mu g/(cm^2 * 24\ h)$
[b]TSR/buspirone HCl = 99%/1% (w/w)
[c]TSR/buspirone free; base = 99.1%/0.9% (w/w)
[d]NACOR 72-9965/buspirone HCl 99%/1% (w/w)

TABLE 5

| | No. | In vitro Permeation of Buspirone[a] | | |
|---|---|---|---|---|
| Skin | Cells | TSR/salt[b] | TSR/base[c] | NACOR/salt[d] |
| 1 | 5 | 15.11 ± 2.42 | 71.48 ± 2.94 | 56.13 ± 4.59 |
| 2 | 5 | 6.57 ± 0.58 | 43.76 ± 7.02 | 34.08 ± 1.71 |
| 3 | 5 | 9.38 ± 1.78 | 63.17 ± 2.27 | 32.30 ± 6.35 |
| 4 | 5 | 13.49 ± 3.46 | 67.81 ± 4.81 | 48.82 ± 6.87 |
| Total | 20 | 11.14 ± 4 05 | 61.55 ± 11.77 | 42.83 ± 11.35 |

[a]Mean ± SD, $\mu g/(cm^2 * 24\ h)$
[b]TSR/buspirone HCl = 98%/2% (w/w)
[c]TSR/buspirone free base = 98.2%/1.8% (w/w)
[d]NACOR 72-9965/buspirone HCl 98%/2% (w/w)

TABLE 6

| | | In vitro Permeation of Buspirone[a] | | |
|---|---|---|---|---|
| Skin | No. Cells | DURO-TAK/salt[b] | DURO-TAK/base[c] | NACOR/salt[d] |
| 1 | 5 | 15.0 ± 1.3 | 76.5 ± 5.3 | 31.8 ± 8.8 |
| 2 | 5 | 11.2 ± 2.2 | 87.3 ± 13.5 | 24.5 ± 7.2 |
| 3 | 5 | 8.9 ± 2.0 | 66.7 ± 7.1 | 28.3 ± 3.8 |
| 4 | 5 | 13.0 ± 1.2 | 62.5 ± 30.3 | 28.2 ± 6.0 |
| Total | 20 | 12.3 ± 3.1 | 73.2 ± 18.6 | 28.2 ± 6.7 |

[a]Mean ± SD, $\mu g/(cm^2 * 24\ h)$
[b]DURO-TAK 2516/buspirone HCl = 98%/2% (w/w)
[c]DURO-TAK/buspirone free base = 98.2%/1.8% (w/w)
[d]NACOR 72-9965/buspirone HCl 98%/2% (w/w)

Permeation from the matrix prepared with the salt form of the drug in the water-based adhesive was two to four times that obtained from the matrix prepared with the salt form of the drug in the organic solvent-based adhesive. In addition, permeation from the matrix prepared with the salt form of the drug in the water-based adhesive was comparable to permeation from the matrix prepared with the free base in the organic solvent-based adhesives. The results of this example demonstrate delivery of a hydrophilic salt form of a basic drug with a water-based adhesive matrix.

EXAMPLE 4

Lidocaine is an analgesic drug that is pharmaceutically approved in both the hydrochloride salt and free base forms. Pressure sensitive matrix systems with lidocaine free base and lidocaine HCl were prepared in an organic solvent-based acrylic adhesive, DURO-TAK 2516, at concentrations equivalent to 1%(w/w) of the HCl salt. The HCl salt did not dissolve completely in the organic solvent-based adhesive, and the final dried cast was a dispersion with visible solid drug crystals in the adhesive matrix. A matrix system with lidocaine HCl at 1% (w/w) was prepared in a water-based acrylic adhesive, NACOR 72-9965. The HCl salt dissolved completely in this adhesive solution, and the matrix was visibly free of drug crystals. The results of in vitro skin flux experiments using these systems are summarized in Table 7.

TABLE 7

| Skin | No Cells | In vitro Permeation of Lidocaine[a] | | |
|------|----------|-------------|-------------|-------------|
|      |          | TSR/salt[b] | TSR/base[c] | NACOR/salt[d] |
| 1 | 5 | 2.97 ± 0.35 | 24.01 ± 2.53 | 12.14 ± 1.87 |
| 2 | 5 | 6.75 ± 2.24 | 23.15 ± 2.76 | 11.11 ± 2.16 |
| 3 | 5 | 6.49 ± 1.77 | 33.30 ± 2.10 | 14.73 ± 3.31 |
| 4 | 5 | 10.07 ± 2.99 | 32.73 ± 2.32 | 21.34 ± 2.32 |
| Total | 20 | 6.57 ± 3.20 | 28.30 ± 5.35 | 14.83 ± 4.68 |

[a]Mean ± SD, $\mu g/(cm^2 \ast 24\ h)$
[b]TSR/lidocaine HCl = 99%/1% (w/w)
[c]TSR/lidocaine free base = 99.14%/0.86% (w/w)
[d]NACOR 72-9965/lidocaine HCl 99%/1% (w/w)

Permeation with the matrix prepared with the salt form of the drug in the water-based adhesive was greater than that obtained with the matrix prepared with the salt form of the drug in the organic solvent-based adhesive and was comparable to permeation with the free base form of the drug in the organic solvent-based adhesive. These results demonstrate delivery of the hydrophilic salt form of a basic drug with a water-borne pressure sensitive adhesive matrix.

EXAMPLE 5

Clonidine is an antihypertensive drug approved for oral administration as the hydrochloride salt and for transdermal delivery as the free base. Conversion to the free base form was required because the salt form was insoluble in the organic solvent-based polyisobutylene adhesive used in the transdermal patch. A pressure sensitive adhesive matrix system with clonidine free base was prepared in an organic solvent-based polyisobutylene adhesive, 33% VISTANEX MM L-100/66% VISTANEX LM-MH (Exxon, Houston, Tex.), at a concentration equivalent to 2% (w/w) of the HCl salt. Another matrix system with clonidine HCl at 2% (w/w) was prepared in a water-based polyisobutylene adhesive, 33% LORD PIB 500/66% LORD BUTYL 100 (Lord Corporation, Pompano Beach, Fla.). The HCl salt dissolved completely in this water-based adhesive solution, and the matrix was visibly free of drug crystals. The results of in vitro skin flux experiments using the systems are summarized in Table 8.

TABLE 8

| Skin | No. Cells | In vitro Permeation of Clinidine[a] | |
|------|-----------|-------------------|------------------|
|      |           | VISTANEX/base[b] | LORD/salt[c] |
| 1 | 5 | 8.6 ± 5.7 | 13.2 ± 6.1 |
| 2 | 4 | 14.0 ± 4.0 | 7.2 ± 0.9 |
| Total | 9 | 11.0 ± 5.5 | 10.5 ± 5.3 |

[a]Mean ± SD, $\mu g/(cm^2 \ast 24\ h)$
[b]VISTANEX L-100/LM-MH/clonidine = 33.1/65.2/1.7% (w/w)
[c]LORD PIB-500/BL-100/clonidine HCl = 33%/65%/2% (w/w)

Permeation with the matrix prepared with the salt form of the drug in the water-based adhesive was comparable to that obtained with the matrix prepared with the free base form of the drug in the organic solvent-based adhesive. These results demonstrate delivery of a hydrophilic salt form of a basic drug with a water-based pressure sensitive adhesive matrix.

EXAMPLE 6

Permeation enhancers can optionally be incorporated into a water-based adhesive matrix system, as shown in this example for an acidic drug (diclofenac sodium) and two basic drugs (buspirone HCl and clonidine HCl). Pressure sensitive adhesive matrix systems were prepared with the salt forms of these drugs at a concentration of 2% (w/w) in a water-based acrylic adhesive, NACOR 72-9965. Additional systems were also prepared with 2.5% (w/w) of a non-ionic permeation enhancer, lauryl lactate (CERAPHYL 31; ISP, Van Dyk, N.J.). The results of in vitro skin flux experiments with these systems are shown in Tables 9–11.

TABLE 9

| Skin | No. Cells | In vitro Permeation of Diclofenac[a] | |
|------|-----------|---------------|-------------------------|
|      |           | NACOR/salt[b] | NACOR/salt/enhancer[c] |
| 1 | 5 | 20.73 ± 1.72 | 30.47 ± 8.23 |
| 2 | 5 | 2.13 ± 0.44 | 3.40 ± 0.82 |
| Total | 10 | 11.43 ± 9.87 | 16.94 ± 15.29 |

[a]Mean ± SD, $\mu g/(cm^2 \ast 24\ h)$
[b]NACOR 72-9965/diclofenac sodium = 98%/2% (w/w)
[c]NACOR 72-9965/diclofenac sodium/lauryl lactate = 95.5%/2%/2.5% (w/w)

TABLE 10

| Skin | No Cells | In vitro Permeation of Buspirone[a] | |
|------|----------|---------------|-------------------------|
|      |          | NACOR/salt[b] | NACOR/salt/enhancer[c] |
| 1 | 5 | 2.60 ± 0.97 | 4.20 ± 1.76 |
| 2 | 5 | 37.91 ± 2.50 | 48.28 ± 3.60 |
| Total | 10 | 20.26 ± 18.70 | 26.24 ± 23.38 |

[a]Mean ± SD, $\mu g/(cm^2 \ast 24\ h)$
[b]NACOR 72-9965/buspirone HCl = 98%/2% (w/w)
[c]NACOR 72-9965/buspirone HCl/lauryl lactate = 95.5%/2%/2.5% (w/w)

TABLE 11

| Skin | No. Cells | In vitro Permeation of Clonidine[a] | |
|---|---|---|---|
| | | NACOR/salt[b] | NACOR/salt/enhancer[c] |
| 1 | 5 | 3.0 ± 0.7 | 3.7 ± 1.1 |
| 2 | 5 | 12.8 ± 5.7 | 15.4 ± 9.4 |
| Total | 10 | 8.5 ± 6.6 | 9.6 ± 8.8 |

[a]Mean ± SD, $\mu g/(cm^2 \cdot 24\ h)$
[b]NACOR 72-9965/clonidine HCl = 98%/2% (w/w)
[c]NACOR 72-9965/clonidine HCl/lauryl lactate = 95.5%/2%/2.5% (w/w)

The results of these experiments illustrate that effective amounts of permeation enhancers can be incorporated advantageously into water-based adhesive matrix systems.

EXAMPLE 7

An additional example of the incorporation of a permeation enhancer in a water-based adhesive was prepared using buspirone HCl as a model drug and sucrose laurate, a known permeation enhancer. Pressure sensitive adhesive matrix systems were prepared with buspirone HCl at a concentration of 2% (w/w) and sucrose laurate at 5% (w/w) (Ryoto LWA 1570; Mitubishi-Kagaku Foods Corporation, Tokyo, Japan) in a water-based acrylic adhesive, NACOR 72-9965. The results of in vitro skin flux experiments with this system are shown in Table 12.

TABLE 12

| Skin | No. Cells | In Vitro Permeation of Buspirone[a] NACOR/salt/enhancer[b] |
|---|---|---|
| 1 | 5 | 23.0 ± 3.5 |
| 2 | 5 | 14.2 ± 1.0 |
| 3 | 5 | 53.6 ± 8.9 |
| 4 | 5 | 23.7 ± 6.6 |
| Total | 20 | 28.6 ± 16.2 |

[a]Mean ± SD, $\mu g/(cm^2 \cdot 24\ h)$
[b]NACOR 72-9965/buspirone HCl/Ryoto LWA 1570 = 93/2/5%

These results further illustrate that permeation enhancers may be readily incorporated into a water-based adhesive matrix system.

We claim:

1. A method of transdermally delivering a hydrophilic salt form of a drug comprising the steps of:
  (a) providing a pressure sensitive adhesive matrix patch device comprising
    (i) a drug-containing adhesive matrix layer comprising a water-based polyisobutylene adhesive having dissolved therein an effective amount of said hydrophilic salt form of said drug, wherein said hydrophilic salt form of said drug is selected from the group consisting of diclofenac sodium, sodium cromolyn, sodium acyclovir, sodium ampicillin, ketorolac tromethamine, amiloride HCl, ephedrine HCl, loxapine HCl, thiothixene HCl, trifluoperizine HCl, naltrexone HCl, naloxone HCl, nalbuphine HCl, buspirone HCl, bupriprion HCl, phenylephrine HCl, tolazoline HCl, chlorpheniramine maleate, phenylpropanolamine HCl, clonidine HCl, dextromethorphan HBr, metoprolol succinate, metoprolol tartrate, epinephrine bitartrate, ketotofin fumarate, atropine sulfate, fentanyl citrate, apomorphine sulfate, propranolol HCl, pindolol HCl, lidocaine HCl, tetracycline HCl, oxytetracycline HCl, tetracaine HCl, dibucaine HCl, terbutaline sulfate, scopolamine HBr, and brompheniramine maleate, and optionally an effective amount of a permeation enhancer, a proximal surface of said layer adapted to adhere to the skin and a distal surface of said layer adapted to adhere to a backing layer, and
    (ii) a backing layer that is substantially impermeable to said drug laminated to said distal surface; and
  (b) contacting a selected area of the skin with said matrix patch device such that said proximal surface of said drug-containing adhesive matrix layer adheres to and is in drug transfer relationship with said selected area of the skin.

2. The method of claim 1 wherein said drug is ketorolac tromethamine.

3. The method of claim 1 wherein said drug is diclofenac sodium.

4. The method of claim 1 wherein said drug is buspirone HCl.

5. The method of claim 1 wherein said drug is lidocaine HCl.

6. The method of claim 1 wherein said drug is clonidine HCl.

7. The method of claim 1 wherein wherein said drug-containing adhesive layer comprises said effective amount of said permeation enhancer.

8. A method of transdermally delivering diclofenac sodium comprising the steps of:
  (a) providing a pressure sensitive adhesive matrix patch device comprising
    (i) a drug-containing adhesive matrix layer comprising a water-based adhesive selected from the group consisting of polyisobutylene and acrylic adhesives having dissolved therein an pharmaceutically effective amount of diclofenac sodium, and optionally an effective amount of a permeation enhancer, a proximal surface of said layer adapted to adhere to the skin and a distal surface of said layer adapted to adhere to a backing layer, and
    (ii) a backing layer that is substantially impermeable to diclofenac sodium laminated to said distal surface; and
  (b) contacting a selected area of the skin with said matrix patch device such that said proximal surface of said drug-containing adhesive matrix layer adheres to and is in drug transfer relationship with said selected area of the skin.

9. The method of claim 8 wherein said drug-containing adhesive matrix layer comprises said effective amount of said permeation enhancer.

10. A pressure sensitive adhesive matrix patch device for transdermally delivering a hydrophilic salt form of a drug comprising
  (a) a drug-containing adhesive matrix layer comprising a water-based polyisobutylene adhesive having dissolved therein an effective amount of said hydrophilic salt form of said drug, wherein said hydrophilic salt form of said drug is selected from the group consisting of diclofenac sodium, sodium cromolyn, sodium acyclovir, sodium ampicillin, ketorolac tromethamine, amiloride HCl, ephedrine HCl, loxapine HCl, thiothixene HCl, trifluoperizine HCl, naltrexone HCl, naloxone HCl, nalbuphine HCl, buspirone HCl, bupriprion HCl, phenylephrine HCl, tolazoline HCl, chlorpheniramine maleate, phenylpropanolamine HCl, clonidine HCl, dextromethorphan HBr, metoprolol succinate, metoprolol tartrate, epinephrine bitartrate, ketotofin fumarate, atropine sulfate, fentanyl citrate, apomorphine sulfate, propranolol HCl, pindolol HCl, lidocaine HCl, tetracycline HCl, oxytetracycline HCl, tetracaine HCl, dibucaine HCl, terbutaline sulfate, scopolamine HBr, and brompheniramine maleate, and optionally an effective amount of a permeation enhancer, a proximal surface of said layer adapted to adhere to the skin and a distal surface of said layer adapted to adhere to a backing layer; and (b) a backing layer that is substantially impermeable to said drug laminated to said distal surface.

11. The device of claim 10 wherein wherein said drug is ketorolac tromethamine.

12. The device of claim 10 wherein said drug is diclofenac sodium.

13. The device of claim 10 wherein said drug is buspirone HCl.

14. The device of claim 10 wherein said drug is lidocaine HCl.

15. The device of claim 10 wherein said drug is clonidine HCl.

16. The device of claim 10 wherein said drug-containing adhesive layer comprises said effective amount of said permeation enhancer.

17. A pressure sensitive adhesive matrix patch device for transdermally delivering diclofenac sodium comprising (a) a drug-containing adhesive matrix layer comprising a water-based adhesive selected from the group consisting of polyisobutylene and acrylic adhesives having dissolved therein a pharmaceutically effective amount of diclofenac sodium, and optionally an effective amount of a permeation enhancer, a proximal surface of said layer adapted to adhere to the skin and a distal surface of said layer adapted to adhere to a backing layer, and (b) a backing layer that is substantially impermeable to diclofenac sodium laminated to said distal surface.

18. The device of claim 17 wherein said drug-containing adhesive matrix layer comprises said effective amount of said permeation enhancer.

* * * * *